United States Patent
Olt

(10) Patent No.: US 11,378,566 B2
(45) Date of Patent: Jul. 5, 2022

(54) METHOD FOR DETERMINING AMMONIUM

(71) Applicant: MERCK PATENT GMBH, Darmstadt (DE)

(72) Inventor: Ralf Olt, Luetzelbach-Seckmauern (DE)

(73) Assignee: MERCK PATENT GMBH, Darmstadt (DE)

( * ) Notice: Subject to any disclaimer, the term of this patent is extended or adjusted under 35 U.S.C. 154(b) by 450 days.

(21) Appl. No.: 16/335,004

(22) PCT Filed: Sep. 18, 2017

(86) PCT No.: PCT/EP2017/073384
§ 371 (c)(1),
(2) Date: Mar. 20, 2019

(87) PCT Pub. No.: WO2018/054797
PCT Pub. Date: Mar. 29, 2018

(65) Prior Publication Data
US 2019/0265219 A1    Aug. 29, 2019

(30) Foreign Application Priority Data

Sep. 20, 2016  (EP) .................................... 16189652

(51) Int. Cl.
| | |
|---|---|
| *G01N 33/18* | (2006.01) |
| *G01N 21/80* | (2006.01) |
| *G01N 21/78* | (2006.01) |
| *G01N 31/22* | (2006.01) |

(52) U.S. Cl.
CPC ......... *G01N 33/1813* (2013.01); *G01N 21/78* (2013.01); *G01N 21/80* (2013.01); *G01N 31/22* (2013.01)

(58) Field of Classification Search
CPC .... G01N 33/1813; G01N 21/78; G01N 21/80; G01N 31/22
See application file for complete search history.

(56) References Cited

U.S. PATENT DOCUMENTS

| | | | | |
|---|---|---|---|---|
| 4,223,089 | A * | 9/1980 | Rothe | C07D 217/10 435/805 |
| 4,507,388 | A * | 3/1985 | Tabacco | C12Q 1/58 435/12 |
| 5,620,900 | A * | 4/1997 | Tanzer | G01N 31/22 435/12 |

OTHER PUBLICATIONS

Phillip L Searle: "The berthelot or indophenol reaction and its use in the analytical chemistry of nitrogen. A review", ANALYST, Jan. 1, 1984 (Jan. 1, 1984), pp. 549-568, XP055429658.
Philip L. Searle: "The Berthelot or Indophenol Reaction and Its Use in the Analytical Chemistry of Nitrogen", ANALYST, vol. 109, May 1984 (May 1, 1984), pp. 549-568.

(Continued)

*Primary Examiner* — Brian R Gordon
*Assistant Examiner* — Dwan A Gerido
(74) *Attorney, Agent, or Firm* — Millen, White, Zelano & Branigan, PC; Ryan Pool

(57) ABSTRACT

The invention relates to a method for determining ammonium or ammonia in aqueous samples in accordance with the known Berthelot method, wherein the risk of incorrectly low results is greatly reduced by additionally measuring the extinction in the absorption range of the nitroprusside used as a catalyst.

13 Claims, 2 Drawing Sheets

(56) References Cited

OTHER PUBLICATIONS

Patton C J et al.: "Spectrophotometric and Kinetics Investigation of the Berthelot Reaction for the Determination of Ammonia", Analytical Chemistry, American Chemical Society, US, vol. 49, No. 3, Mar. 1, 1977 (Mar. 1, 1977), pp. 464-469, XP000670548, ISSN: 0003-2700.

Michael D. Krom: "Spectrophotometric Determination of Ammonia: A Study of a Modified Berthelot Reaction Using Salicylate and Dichloroisocyanurate", ANALYST, vol. 105, No. 1249, Apr. 1980 (Apr. 1, 1980), pp. 305-316.

\* cited by examiner

METHOD FOR DETERMINING AMMONIUM

The present invention relates to a method for the determination of ammonium or ammonia in aqueous samples by the known Berthelot method, where the risk of incorrectly low results is greatly reduced by the additional measurement of the extinction in the absorption region of the nitroprusside employed as catalyst.

PRIOR ART

Ammonium nitrogen ($NH_4$—N) is present in many above-ground water courses, in some ground waters, and in domestic and many commercial waste waters (source: DIN 38406-5, ISO 7150-1).

Ammonia is toxic to fish, even in low concentrations. Ammonium contents in water of 0.5 to 1 mg/l are therefore, depending on the pH of the water, classified as hazardous to fish. At ammonium contents of above 1 mg/l, a water course is typically unsuitable for fishery purposes.

Ammonium compounds accordingly belong to the water-endangering substances, limit values can be found in many regulations. Monitoring of the ammonium content in water and waste-water samples is therefore vitally necessary on a regular basis.

Standardised methods for the determination of the ammonium content are frequently used. These include, inter alia, the Berthelot method.

The method is carried out at an alkaline pH, at which ammonium is in the form of ammonia ($NH_3$).

In the first step of the Berthelot method, ammonia reacts with hypochlorite to give monochloramine.

In the next step, the monochloramine formed reacts with a phenol derivative in the presence of the catalyst nitroprusside to give a chloroquinone monoimine. In principle, various compounds are suitable as the phenol derivative. For example, salicylates, thymol or 2-chlorophenol are frequently used in the official methods.

In the final reaction step, the chloroquinone monoimine formed reacts with a further molecule of the phenol derivative to give a corresponding indophenol.

The blue colour of the indophenol formed is measured photometrically (at a wavelength in the region of absorption maximum) and in certain measurement ranges correlates with the ammonium content of the sample.

The complete reaction mechanism has not been unambiguously clarified to date and proceeds via many intermediates.

Further information and details on the Berthelot method can be found, for example, in Philip L. Searle, Analyst, May 1984, Vol 109, pages 549-568 "The Berthelot or Indophenol Reaction and Its Use in the Analytical Chemistry of Nitrogen" or Michael D. Krom, Analyst, April 1980, Vol. 105 No. 1249, pages 305-316 "Spectrophotometric Determination of Ammonia:

A Study of a Modified Berthelot Reaction Using Salicylate and Dichloroisocyanurate"

The method can in principle be used for various measurement ranges if the sample/reagent ratios are adapted correspondingly or the sample is pre-diluted.

Ammonium tests which use this method are also available from various manufacturers in the form of ready-to-use test sets.

The method described above has the disadvantage that the blue colour formed only correlates with the ammonium content in certain concentration ranges of the ammonium to be determined.

In general, the measurement signal (extinction) of the photometric measurement increases with increasing ammonium content of the sample.

It has been found in practice that the measurement signal, i.e. the extinction, drops again at very high ammonium concentrations of the sample (see FIG. 1). The cause has not been ambiguously identified to date. It is thought that the reaction mechanism no longer proceeds completely at unfavourable analyte/reagent ratios. A pH shift due to excessive monocloramine formed may also be responsible for this. A reliable report of the ammonium content is not possible in this case and in the worst case a significant misestimation of the ammonium content may occur, with serious effects on the environment.

The standards and test set manufacturers therefore prescribe that further analyses with diluted sample (various pollution steps) should be carried out in addition to analysis of the sample in order to check the plausibility of the measurement result. This is inconvenient and time-consuming for the user.

OBJECT OF THE INVENTION

The object of the present invention is therefore to provide a method for the determination of the ammonium content of aqueous samples which, besides the measurement result of a single measurement, also supplies directly information on the plausibility of this measurement result without the need to measure further samples, for example as part of a dilution series.

ACHIEVEMENT OF THE OBJECT

It has been found that the plausibility of a measurement of the ammonium content by the Berthelot method can be checked if, besides the measurement of the extinction in the absorption region of the blue indole dye formed, a measurement of the extinction in the absorption region of the nitroprusside employed as catalyst is additionally carried out on the sample. If the measurement in the absorption region of the nitroprusside employed as catalyst indicates that sufficient nitroprusside is present, the result of the ammonium determination is plausible. If the measurement in the absorption region of nitroprusside indicates that little or no catalyst is present, the plausibility of the result of the ammonium determination must be doubted.

In this way, the plausibility of the actual measurement result of the ammonium determination can be checked by means of an additional measurement of the extinction in the absorption region of nitroprusside carried out directly on the same sample. Further measurements of dilutions of the sample are normally unnecessary.

The present invention therefore relates to a method for the determination of the ammonium content of aqueous samples in which
a) a chlorinating agent, a phenol derivative and nitroprusside are added to the sample at an alkaline pH,
b) the extinction of the mixture obtained in step a), optionally after waiting for a reaction time, is determined in the absorption region of the blue dye formed and in the absorption region of nitroprusside.

In a preferred embodiment, the chlorinating agent is dichloroisocyanuric acid.

In a preferred embodiment, the phenol derivative is 2-chlorophenol or thymol, particularly preferably 2-chlorophenol.

In a preferred embodiment, the alkaline pH in step a) is generated by addition of sodium hydroxide solution.

In a preferred embodiment, the pH in step a) is between pH 11 and pH 12. The optimum pH for a sample is dependent on the phenol derivative used, in the case of 2-chlorophenol, for example, a pH between pH 11.5 and 11.8 is preferred.

In a preferred embodiment, the measurement of the extinction in step b) is carried out using a spectrophotometer.

In a preferred embodiment, the determinations of the extinctions are carried out by carrying out a measurement in the wavelength range between 350 and 450 nm and a measurement in the wavelength range between 600 and 800 nm.

The present invention furthermore relates to a method for the determination of the plausibility of the measurement result of a determination of the ammonium content of aqueous samples in which the measurement is carried out in accordance with the method according to the invention for the determination of the ammonium content of aqueous samples, i.e. by
 a) preparation of an aqueous sample having an alkaline pH and addition of a chlorinating agent, a phenol derivative and nitroprusside to this sample,
 b) determination of the extinction of the mixture prepared in step a), optionally after waiting for a reaction time, in the absorption region of the blue dye formed and in the absorption region of nitroprusside,
and where the extinction of the sample in the absorption region of the blue dye formed is only regarded as a plausible measurement result if the extinction in the absorption region of nitroprusside is above a threshold value to be determined in advance.

In a preferred embodiment, the threshold value corresponds to the extinction that would be caused in this mixture by half of the nitroprusside present in the mixture from step a) if this mixture contained no ammonium.

In a preferred embodiment, the threshold value is determined by
 i. provision of a blank value sample which contains no ammonium, having an alkaline pH, and addition of a chlorinating agent, a phenol derivative and nitroprusside to this blank value sample so that it has the same composition and concentration with respect to pH, chlorinating agent, phenol derivative and nitroprusside as the mixture whose extinction is determined in step b)
 ii. determination of the extinction of the blank value sample in the absorption region of nitroprusside, where the extinction of nitroprusside in step b) and step ii is preferably determined at the same wavelength
 iii. calculation of the threshold value by halving the extinction value determined in step ii).

In a preferred embodiment, the chlorinating agent is dichloroisocyanuric acid.

In a preferred embodiment, the phenol derivative is 2-chlorophenol or thymol, particularly preferably 2-chlorophenol.

In a preferred embodiment, the alkaline pH in step a) is produced by addition of sodium hydroxide solution.

In a preferred embodiment, the pH in step a) is between pH 11 and pH 12. The optimum pH for a sample is dependent on the phenol derivative used, in the case of 2-chlorophenol, for example, a pH between pH 11.5 and 11.8 is preferred.

In a preferred embodiment, the determination of the extinction of nitroprusside in step b) and step ii is carried out at the absorption maximum of nitroprusside.

The individual aspects or subject-matters of the invention described above can also be achieved in any desired combination of two or more aspects or subject-matters.

Figure 1:
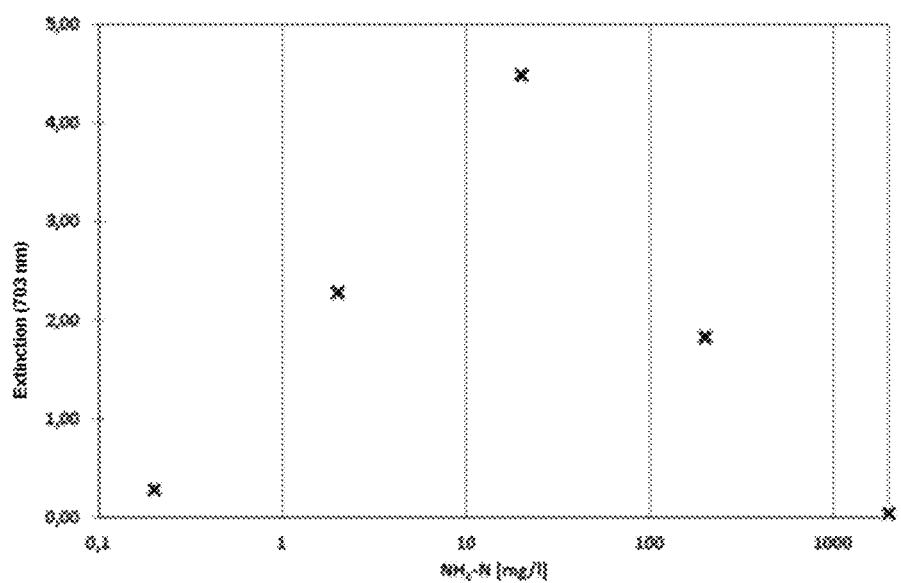
FIG. 1 shows the measured extinction of the in the case of the determination of the ammonium content of a sample by the Berthelot method for various ammonium concentrations.

In accordance with the invention, an aqueous sample is a sample which contains one or typically more components dissolved in water. In general, the aqueous sample contains no further solvents apart from water. However, it may contain up to 20% of one or more water-miscible solvents, such as, for example, ethanol. An aqueous sample can be a water sample, a food or drink, or a body fluid. The aqueous sample is very preferably a water sample, such as, for example, a sample taken from a water course, a waste-water sample, a ground water sample, a tap water sample, a sample of water fed to an industrial process or discharged from an industrial process as waste water, etc.

The ammonium content of a sample is a sample's content of ammonium compounds present which can be converted into ammonia when the sample is rendered alkaline or are in the form of ammonia in an alkaline sample. The sample is typically brought here to a pH between pH 10 and pH 13.5, preferably between 11 and 12. This can be carried out using bases or hydroxide solutions, for example using aqueous LiOH, NaOH, KOH solution, preferably using sodium hydroxide solution. Examples of ammonium compounds are therefore ammonium salts, ammonium hydroxide and ammonia.

In the determination of the ammonium content by the Berthelot method, a chlorinating agent, a phenol derivative and nitroprusside as catalyst are added to the sample in the alkaline region, and a certain time, which is generally between 5 and 30 minutes, preferably between 10 and 20 minutes, is typically awaited in order that the detection reaction can take place. A blue-coloured indophenol forms over several reaction steps. The extinction determined in the absorption region of the indophenol correlates with the ammonium content of the sample in certain measurement ranges known to the person skilled in the art. The measurement of the ammonium content can be carried out in accordance with the invention using any variant of the Berthelot method in which nitroprusside is used as catalyst.

Suitable chlorinating agents are, for example, sodium hypochlorite and dichloroisocyanurate (DIC) or dichloroisocyanuric acid. Dichloroisocyanuric acid is particularly preferred.

Suitable phenol derivatives are, for example, phenol or 2-substituted phenols, such as 2-chlorophenol, thymol or salicylates.

For example, it is possible to use the method described in DIN 38406/5, in which dichloroisocyanuric acid is used instead of the hypochlorite often used and sodium salicylate is used instead of phenol.

Nitroprusside, also called sodium nitroprusside, is a complex of the empirical formula $Na_2[Fe(CN)_5NO].2H_2O$.

In order to determine the ammonium content quantitatively, the extinction of the sample after addition of the requisite reagents and after formation of the blue to blue-green indophenol is determined at a certain wavelength in the absorption region of the indophenol. The measurement is typically carried out at the absorption maximum. The quantitative determination can then be carried out with the aid of a calibration curve. This procedure is known to the person skilled in the art. The calibration curve and the wavelength at which the extinction are determined must be determined correspondingly for each reagent combination (type and amount of chlorinating agent, phenol derivative, pH, etc.). Indophenols which have an absorption maximum in the wavelength range between 600 and 800 nm are typically formed in the determination.

The core of the present invention is that the plausibility or also correctness of the result of a measurement of the ammonium content of an aqueous sample by the Berthelot method does not have to be determined as hitherto by complex measurement of dilution series of this sample, but instead can be determined by measurement only of this one sample itself.

To this end, the determination of the ammonium content by the Berthelot method is carried out in accordance with known methods and with conventional reagents known to the person skilled in the art, where the catalyst used is nitroprusside. In addition to the usual measurement of the extinction of the sample in the absorption region, preferably at the absorption maximum, of the indophenol formed, a second measurement is carried out on the same sample in the absorption region of nitroprusside, preferably at about 400 nm The result of the second measurement in the absorption region of nitroprusside allows a statement on the amount of nitroprusside present in the measurement sample. It has been found that, at very high contents of ammonium, which lead to an incorrectly low extinction value in the absorption region of the indophenol, the amount of nitroprusside and thus the extinction in the absorption region of nitroprusside is also very low at the same time. Due to this correlation, the determination of the nitroprusside content in the sample allows a direct conclusion on the plausibility of the result of the determination of the ammonium content.

Since the person skilled in the art knows how much nitroprusside has been added to the sample, he is able to draw corresponding conclusions from the result of the measurement in the absorption region of nitroprusside. Typically, it can be assumed that the result of the ammonium determination is plausible if the measurement in the absorption region of nitroprusside shows that at least half of the nitroprusside originally added to the sample is still present as such and thus contributes to the absorption in this region.

However, the determination of the plausibility of the measurement result obtained for the determination of the ammonium content is preferably carried out by comparison of the result of the measurement in the absorption region of nitroprusside with a pre-defined threshold value. If the measurement result is above this threshold value, the result of the determination of the ammonium content of the sample is plausible. If the result of the measurement in the absorption region of nitroprusside is below the threshold value, the plausibility of the result of the determination of the ammonium content of the sample must be doubted and correspondingly checked, for example by measurement of dilution series.

The threshold value can be established by the person skilled in the art by ensuring that sufficient nitroprusside is still present in the mixture to be measured. 40%, preferably about 50%, of the amount of nitroprusside originally added are typically sufficient.

The threshold value is preferably established in advance by provision of a blank value sample which contains no ammonium, adjustment to an alkaline pH and addition of a chlorinating agent, a phenol derivative and nitroprusside to this blank value sample, so that it has the same composition and concentration with respect to pH, chlorinating agent, phenol derivative and nitroprusside as the aqueous sample whose ammonium content is to be determined and to which these reagents have been added. The extinction of the blank value sample is then measured in the absorption region of nitroprusside. The threshold value is then calculated by halving the extinction value. Determinations of the extinction of the nitroprusside in the aqueous sample and in the blank value sample are preferably carried out at the same wavelength.

The performance of photometric measurements is known to the person skilled in the art. The photometric measurement is typically carried out by measurement of the extinction at at least two wavelengths in the range from 300-700 nm. All photometers which are suitable for measurements between 300 nm and 700 nm are suitable for this purpose.

For measurement of the extinction, the aqueous sample is generally introduced into a cell.

In accordance with the invention, a cell is a vessel in which photometric measurements can be carried out. Cells typically consist of quartz, glass or plastic and have at least two plane-parallel side surfaces or are round. The choice of cell and the thickness of the cell allow the extinction to be reduced or increased for the same composition of the sample to be measured.

Besides the reagents for the determination of the ammonium content, further reagents can be added to the aqueous sample before or after the alkalinisation of the sample. This may be necessary, for example, in order to prevent other constituents present in the sample from precipitating out at the high pH values necessary for the determination, or in order to prevent interference with the formation of the indophenol. Examples of reagents of this type are EDTA or trisodium citrate.

The present invention enables a large reduction in the amount of work carried out in the determination of the ammonium content by the Berthelot method. In particular in laboratories in which many samples are measured daily, the amount of work carried out can be reduced greatly. Dilution series only have to be carried out for final clarification if the plausibility check by the method according to the invention shows that the plausibility must be doubted.

The present description enables the person skilled in the art to apply and carry out the invention comprehensively. Even without further comments, it will therefore be assumed that a person skilled in the art will be able to utilise the above description in the broadest scope.

Should anything be unclear, it goes without saying that the cited publications and patent literature should be consulted. Accordingly, the complete disclosure content of all applications, patents and publications mentioned above and below, in particular of the corresponding application EP 16189652.7, filed on 20 Sep. 2016, is incorporated into this application by way of reference.

For better understanding and in order to illustrate the invention, examples are given below. These examples also serve to illustrate possible variants. Owing to the general validity of the inventive principle described, however, the examples are not suitable for reducing the scope of protection of the present application to these alone.

Furthermore, it goes without saying to the person skilled in the art that, both in the examples given and also in the remainder of the description, the component amounts present in the compositions always only add up to 100% by weight or mol-%, based on the entire composition, and cannot exceed this, even if higher values could arise from the percent ranges indicated. Unless indicated otherwise, % data are by weight, with the exception of ratios, which are reproduced in volume amounts, such as, for example, eluents for the preparation of which solvents are used in a mixture in certain volume ratios.

The temperatures given in the examples and description and in the claims are always in ° C.

EXAMPLES

Example in Accordance with the Prior Art

The determination of the ammonium content of samples having a different content of ammonium is carried out in accordance with a ready-to-use test set for the determination of ammonium from Merck. Article number 1147390001 Spectroquant® ammonium cell test is used here. The phenol derivative in this case is 2-chlorophenol. The measurement is carried out at a wavelength of 703 nm. The result is shown in FIG. 1.

It can be seen that the extinction increases up to an ammonium content of about 20 to 30 mg/l. It then drops again in spite of the higher ammonium content. The two measurements at an ammonium content above 100 mg/l essentially give rise to excessively low extinction values.

Example According to the Invention:

TABLE 1

| $NH_4$—N [mg/l] | $A_{703\,nm}$ (indophenol blue) | $A_{397\,nm}$ (nitroprusside) |
| --- | --- | --- |
| 0 | 0.057 | 3.854 |
| 0.2 | 0.279 | 3.921 |
| 2 | 2.281 | 4.227 |
| 20 | 4.487 | 3.733 |
| 200 | 1.828 | 1.124 |
| 2000 | 0.039 | 0.699 |

Figure 2:
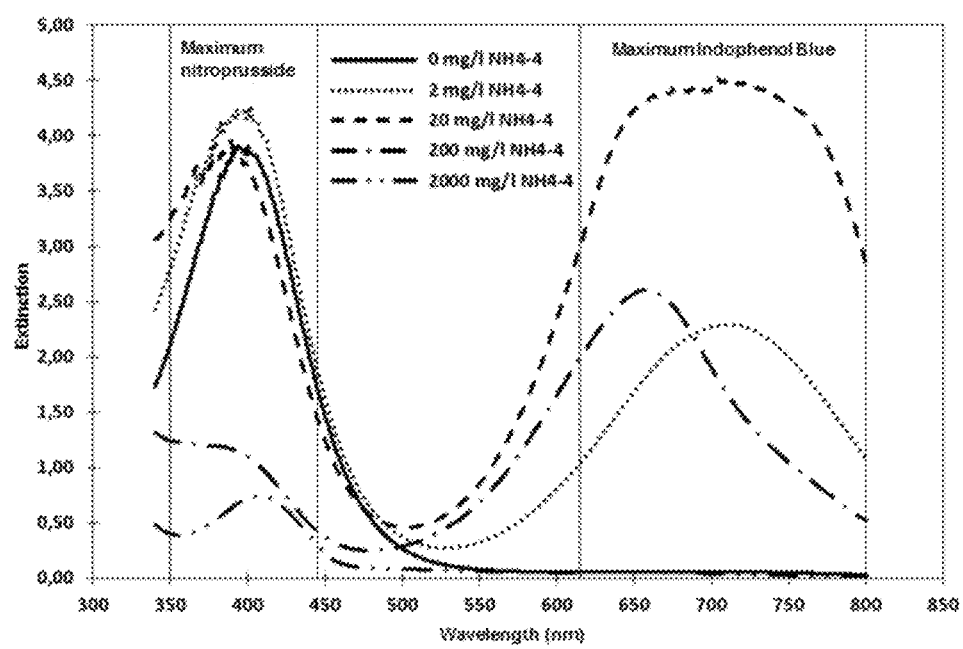
FIG. 2 shows the measured extinction in the case of the determination of the ammonium content of a sample by the Berthelot method for various ammonium concentrations in the absorption region of the blue dye formed and in the absorption region of nitroprusside.

Threshold value 1: $A_{703\,nm} \leq 2.400$
Threshold value 2: $A_{397\,nm} \geq 3.400$ The values in Table 1 and the curves shown in FIG. 2 were determined with the aid of a ready-to-use test set for the determination of ammonium from Merck. Article number 1147390001 Spectroquant® ammonium cell test was used here. The test set is suitable for samples within the measurement range 0.010-2.000 mg/l of $NH_4$—N. Standard samples having a content of 0/0.20/2.00/20.0/200 and 2000 mg/l of $NH_4$—N were analysed. The standard substance employed was ammonium chloride $NH_4Cl$. In order to prepare a solution of 2000 mg/l of NH4-N, 7.638 g of $NH_4Cl$ must be dissolved in 1000 ml of dist. water. The other concentrations shown are prepared from this solution by dilution with dist. water. The test set is distinguished by the fact that the reagents required are in ready-to-use form. The measurements are carried out in so-called round cells having a diameter of 16 mm. The round cell already contains 1.5 ml of a reagent. This reagent contains the sodium hydroxide as well as 2-chlorophenol as phenol derivative. Both components have been dissolved in dist. water.

In the first reaction step, 5.0 ml of sample or standard solution are added to the reagent already present in the round cell and mixed. In the second reaction step, a solid reagent is added using a measuring spoon and dissolved and mixed homogeneously with shaking. The solid reagent comprises the other requisite reaction components nitroprusside and dichloroisocyanuric acid as well as fillers.

When all components have been homogeneously mixed with one another, a reaction time of 15 minutes begins.

After expiry of the 15 minutes, the extinction of the round cell is measured in a spectrophotometer at 703 nm and 397 nm. The measurement is carried out against a reference cell of the same type filled with dist. water.

The measurement at 703 nm shows the extinction of the indophenol formed under the reaction conditions present (pH and reaction time), the measurement at 397 nm shows the extinction of nitroprusside after completion of the reaction under the reaction conditions present (pH and reaction time).

It can be seen that the extinction of the indophenol increases proportionally in the measurement range from 0.010-2.000 mg/l of $NH_4$—N indicated. A further increase in the extinction of the indophenol also occurs at a concentration of 20 mg/l of $NH_4$—N. This increase is not proportional to the concentration of the $NH_4$—N. At 200 mg/l of $NH_4$—N, the extinction at 703 nm is below the extinction of the standard having a content of 2 mg/l of $NH_4$—N. In the extreme case, this would lead to the misinterpretations outlined. In the case of the measurement at 397 nm carried out at the same time for detection of the nitroprusside present, it can be seen that the extinction drops considerably at very high concentrations. A linked interpretation of the measurements at the two wavelengths now enables a plausibility rule to be set up. This could be as follows for the example shown:

measurement plausible if extinction at 703 nm<2.400 A and extinction at 397 nm>3.400 A.

The invention claimed is:

1. A method of measuring ammonium content comprising
   a) preparing a sample having an alkaline pH and adding a chlorinating agent, a phenol derivative and nitroprusside to said sample,
   b) determining an extinction of the mixture prepared in step a) in an absorption region of blue dye formed and in an absorption region of nitroprusside, and wherein the extinction in the adsorption range of the resulting blue dye indicates the ammonium content and the extinction in the range of nitroprusside indicates whether or not the ammonium content measurement is plausible, wherein if an extinction in the absorption region of nitroprusside is above a predetermined threshold value, then the extinction of the sample in the absorption region of the blue dye formed is regarded as a plausible measurement result.

2. The method according to claim 1, wherein the threshold value is determined by
   i. providing a blank value sample, in the form of an aqueous solution which contains no ammonium, having an alkaline pH and adding a chlorinating agent, a phenol derivative and nitroprusside to said aqueous solution so that a resultant composition has the same composition and concentration with respect to pH, chlorinating agent, phenol derivative and nitroprusside as the mixture in step b) whose extinction is determined,
   ii. determining the extinction of the blank value sample in the absorption region of nitroprusside, and iii. calculating the threshold value by halving the extinction value determined in step ii.

3. The method according to claim 2, wherein the chlorinating agent is dichloroisocyanuric acid.

4. The method according to claim 2, wherein the phenol derivative is 2-chlorophenol.

5. The method according to claim 2, wherein the alkaline pH in step a) is generated by addition of sodium hydroxide solution.

6. The method according to claim 2, wherein the pH in step a) is set between pH 11 and pH 12.

7. The method according to claim 2, wherein the determination of the extinction of nitroprusside in step b) and step ii. is in each case carried out at the absorption maximum of nitroprusside.

8. A method of measuring ammonium content comprising
a) adding a chlorinating agent, a phenol derivative and nitroprusside to the sample at an alkaline pH,
b) measuring an extinction of the mixture obtained in step a) in an absorption region of blue dye formed and in an adsorption region of nitroprusside,
wherein from the extinction in the adsorption range of the resulting blue dye indicates the ammonium content and the extinction in the range of nitroprusside indicates whether or not the ammonium content measurement is plausible,
wherein only the presence of at least 50% of the amount of nitroprusside indicates a plausible ammonium content measurement.

9. The method according to claim 8, wherein the chlorinating agent is dichloroisocyanuric acid.

10. The method according to claim 8, wherein the phenol derivative is 2-chlorophenol.

11. The method according to claim 8, wherein the alkaline pH in step a) is generated by addition of a sodium hydroxide solution or wherein the pH in step a) is set between pH 11 and pH 12.

12. The method according to claim 8, wherein the determination of the extinction in step b) is carried out by a spectrophotometer.

13. The method according to claim 8, wherein the determination of the extinction is carried out by a photometric measurement in the wavelength range between 350 and 450 nm and a photometric measurement in the wavelength range between 600 and 800 nm.

* * * * *